United States Patent
Wilson

(10) Patent No.: US 6,197,015 B1
(45) Date of Patent: Mar. 6, 2001

(54) ANGIOGRAPHY CATHETER WITH SECTIONS HAVING DIFFERENT MECHANICAL PROPERTIES

(75) Inventor: James C. Wilson, Queensbury, NY (US)

(73) Assignee: Medi-Dyne Inc., Queensbury, NY (US)

( * ) Notice: Subject to any disclaimer, the term of this patent is extended or adjusted under 35 U.S.C. 154(b) by 0 days.

(21) Appl. No.: 09/208,260

(22) Filed: Dec. 9, 1998

(51) Int. Cl.$^7$ ...................................... A61M 25/00
(52) U.S. Cl. ............................. 604/524; 156/158
(58) Field of Search ........................... 604/264, 523–527, 604/532; 156/158, 296, 304.2, 304.5; 138/156, 170, 171; 285/915

(56) References Cited

U.S. PATENT DOCUMENTS

| | | |
|---|---|---|
| 3,924,632 | 12/1975 | Cook . |
| 3,965,909 | 6/1976 | Waddell et al. . |
| 4,044,765 | 8/1977 | Kline . |
| 4,321,226 | 3/1982 | Markling . |
| 4,323,071 | 4/1982 | Simpson et al. . |
| 4,385,635 | 5/1983 | Ruiz . |
| 4,425,919 | 1/1984 | Alston, Jr. et al. . |
| 4,464,176 | 8/1984 | Wijayarathna . |
| 4,516,972 | 5/1985 | Samson . |
| 4,563,181 | 1/1986 | Wijayarathna et al. . |
| 4,577,543 | 3/1986 | Wilson . |
| 4,596,563 | 6/1986 | Pande . |
| 4,636,346 | 1/1987 | Gold et al. . |
| 4,648,892 | 3/1987 | Kittrell et al. . |
| 4,665,604 | 5/1987 | Dubowik . |
| 4,690,175 | 9/1987 | Ouchi et al. . |
| 4,764,324 | 8/1988 | Burnham . |
| 4,817,613 | 4/1989 | Jaraczewski et al. . |
| 4,836,872 | 6/1989 | Landry et al. . |
| 4,842,590 | 6/1989 | Tanabe et al. . |
| 4,846,814 | 7/1989 | Ruiz . |
| 4,863,442 | 9/1989 | DeMello et al. . |
| 4,886,506 | 12/1989 | Lovgren et al. . |
| 4,898,591 | 2/1990 | Jang et al. . |
| 4,904,431 | 2/1990 | Ouchi et al. . |
| 4,961,731 | 10/1990 | Bodicky et al. . |
| 5,017,259 | 5/1991 | Kohsai . |
| 5,037,404 | 8/1991 | Gold et al. . |
| 5,057,092 | 10/1991 | Webster, Jr. . |
| 5,078,702 | 1/1992 | Pomeranz . |
| 5,147,315 | 9/1992 | Weber . |
| 5,156,155 | 10/1992 | King . |
| 5,160,559 | 11/1992 | Scovil et al. . |
| 5,221,270 | 6/1993 | Parker . |
| 5,234,416 | 8/1993 | Macaulay et al. . |
| 5,254,107 | 10/1993 | Soltesz . |
| 5,279,596 | 1/1994 | Castaneda et al. . |

(List continued on next page.)

FOREIGN PATENT DOCUMENTS

| | | |
|---|---|---|
| 0 334 640 | 9/1989 | (EP) . |
| 2043201 | 10/1980 | (GB) . |
| 2 156 680 | 10/1985 | (GB) . |
| WO 95/13110 | 5/1995 | (WO) . |
| WO 95/15780 | 6/1995 | (WO) . |

*Primary Examiner*—Sharon Kennedy
*Assistant Examiner*—Catherine Serke
(74) *Attorney, Agent, or Firm*—Nixon & Vanderhye P.C.

(57) ABSTRACT

A catheter having at least two lengths of tubular material axially joined together by a scarf joint with no perceptible change in outer diameter at the joint; the scarf joint including a substantially axially oriented seam component between the two lengths of tubular material with the seam visible along the peripheral surfaces of the axially joined sections and extending at an acute angle to the longitudinal axis of the catheter; and wherein one of the at least two lengths of tubular material includes an inner tubular reinforcement layer, wherein the reinforcement layer forms part of the scarf joint.

16 Claims, 2 Drawing Sheets

U.S. PATENT DOCUMENTS

| | | |
|---|---|---|
| 5,308,342 | 5/1994 | Sepetka et al. . |
| 5,312,356 | 5/1994 | Engelson et al. . |
| 5,318,032 | 6/1994 | Lonsbury et al. . |
| 5,358,493 | 10/1994 | Schweich, Jr. et al. . |
| 5,403,292 | 4/1995 | Ju . |
| 5,441,489 | 8/1995 | Utsumi et al. . |
| 5,445,624 | 8/1995 | Jimenez . |
| 5,484,425 | 1/1996 | Fischell et al. . |
| 5,531,721 | 7/1996 | Pepin et al. . |
| 5,542,937 | 8/1996 | Chee et al. . |
| 5,545,149 | 8/1996 | Brin et al. . |
| 5,545,151 | 8/1996 | O'Connor et al. . |
| 5,571,073 | 11/1996 | Castillo . |
| 5,584,821 | 12/1996 | Hobbs et al. . |
| 5,603,705 | 2/1997 | Berg . |
| 5,772,641 * | 6/1998 | Wilson ................. 604/280 |
| 5,836,926 * | 11/1998 | Peterson et al. .............. 604/282 |

* cited by examiner

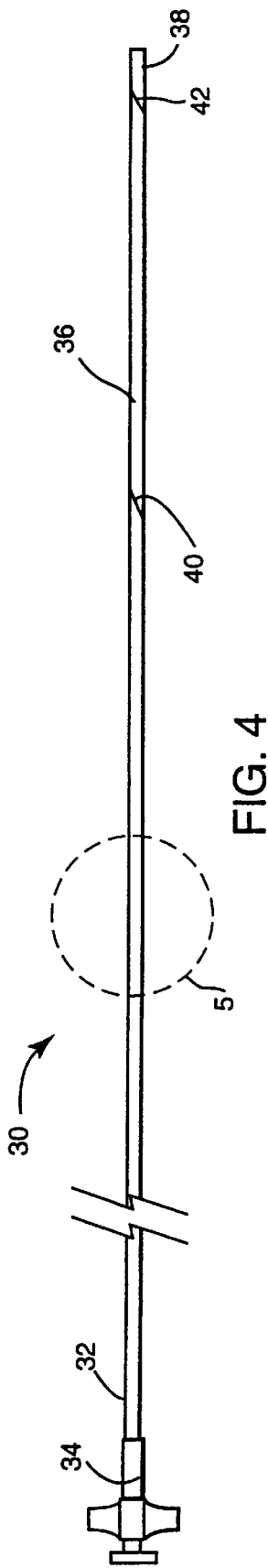
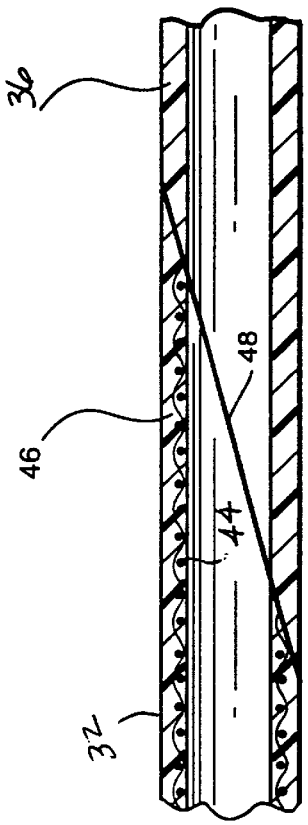
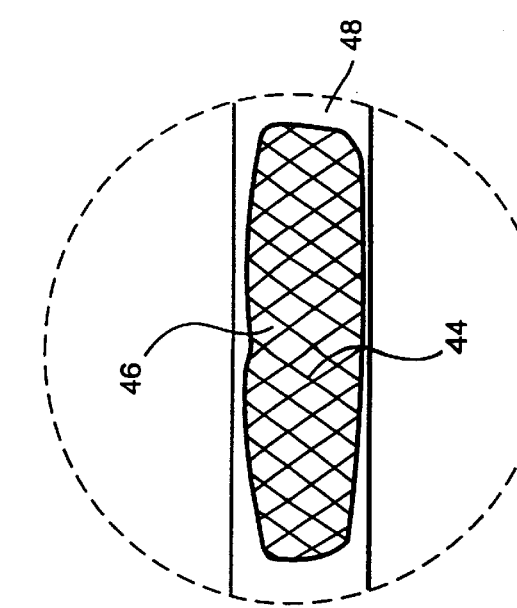
FIG. 4
FIG. 5
FIG. 6

ANGIOGRAPHY CATHETER WITH SECTIONS HAVING DIFFERENT MECHANICAL PROPERTIES

TECHNICAL FIELD

This invention relates generally to catheter constructions, and more particularly, to diagnostic or angiographic catheters with axially joined sections of varying mechanical properties.

BACKGROUND AND SUMMARY OF THE INVENTION

Currently, some diagnostic and therapeutic catheters are manufactured by forming braided tubes of stainless steel fibers or strands over a mandrel. More specifically, the braided tube may be formed about an inner Teflon® liner or tube initially carried on a supporting mandrel. An outer plastic layer may then be extruded about the braided layer to create the catheter body. Current catheter constructions also utilize a transition tip which is not reinforced with braid in order that the tip be softer and more flexible than the remaining portions of the catheter. In some catheter designs, an even softer more flexible tip is bonded to the free end of a relatively soft tubular "transition" tip.

Catheters which incorporate multiple axial sections of the outer layer typically employ butt or lap weld joints to secure such sections together. See, for example, U.S. Pat. Nos. 5,254,107; 4,861,337; 4,793,351; 4,662,404; and 4,391,302. Catheters incorporating either butt or lap type welded joints are not completely satisfactory however. In commonly owned U.S. Pat. No. 5,772,641 (incorporated herein by reference), improved catheter constructions are disclosed which incorporate unique weld configurations which have substantial axial seam components which extend along the axis of the catheter (either parallel to the catheter axis or at an acute angle to the axis). In other words, adjacent outer catheter sections are cut and welded in such a way that they overlap in the longitudinal direction, but without altering the outer diameter of the catheter. This arrangement not only increases surface area at the weld joints to increase bond integrity, but also creates a more desirable transition between axial sections formed of the same materials of different durometer, or different materials with or without the same durometer. The unique joint seam configurations also permit alteration of properties or characteristics of the material in the areas of the joints themselves (thus creating an "intermediate section" or transition area between axially adjacent sections), and this feature is particularly advantageous in areas of the catheter that will be curved or bent in use, in that different stiffness or hardness materials can be used on the inside and outside of the curve. In the '641 patent, however, the unique weld configurations are specified only for the layer of the catheter lying radially outwardly of the braid layer.

In accordance with this invention, further improvements in joint configurations (referred to herein as "scarf joints") are accomplished in a manner which maximizes weld strength while creating even more favorable transitions between tubular sections. In particular, we have now discovered that it is possible to join a braid layer (for example, a stainless steel braided tube), to a non-braided section or to a catheter "tip," utilizing tapered or scarf joints of the type generally disclosed in the '641 patent. More specifically, the tapered or scarf cut can be effected not only in the radially outer plastic layer, but also within the inner braid layer as well. Using heat shrink Teflon®, as is common in tip welding (or other suitable techniques including adhesives with or without the application of heat; passing the assembly through a heated die, etc.), the scarf cut braid layer may be joined or bonded to the axial non-braided tube (or even to another braided tube). In this regard, the stainless wire braid is annealed so that loose ends at the taper or scarf cut do not spring radially outwardly into and/or through the outer plastic layer. Other techniques for keeping the loose ends in place could be employed as well. In addition, however, higher tensile strength wire could be utilized with heat insensitive adhesives.

By employing the scarf cut through the inner braid layer, additional benefits are achieved in terms of varying the flexibility of the catheter along its length, and particularly in transition areas between axial sections.

In an exemplary embodiment of the invention, a relatively stiff braided section is scarf-welded to a moderately stiff non-braided section which, in turn, is scarf welded to a "soft" section or simply tipped with a butt welded soft tip. The number of braided and non-braided sections may vary, however, as dictated by specific applications.

Accordingly, in its broader aspects, the present invention relates to a catheter having at least two lengths of tubular material axially joined together by a scarf joint with no perceptible change in outer diameter at the joint, the scarf joint including a substantially axially oriented seam component between the two lengths of tubular material with the seam visible along the peripheral surfaces of the axially joined sections and extending at an acute angle to the longitudinal axis of the catheter; and wherein one of the at least two lengths of tubular material includes an inner tubular reinforcement layer, wherein the reinforcement layer forms part of the scarf joint.

In another aspect, the invention relates to a catheter having at least two adjacent lengths of tubular material axially overlapped and joined together by a scarf joint, the lengths of tubular material having continuous outer surfaces and a lumen extending along a longitudinal axis, the scarf joint including a seam on the outer surfaces extending more than 0.5 cm in length and at an acute angle to the longitudinal axis of the catheter such that each of the at least two adjacent lengths form substantially half of the catheter along the scarf joint, and wherein the two lengths of material are of different composition with different mechanical properties, thereby establishing an intermediate section having variable properties along the scarf joint; and wherein one of the at least two adjacent lengths of tubular material includes an inner reinforcement layer.

Other objects and advantages of the subject invention will become apparent from the detailed description which follows.

BRIEF DESCRIPTION OF THE DRAWINGS

FIG. 4 is a side elevation, partly broken away, of an angiographic catheter in accordance with the invention;

FIG. 5 is an enlarged detail, with an outer layer partially removed so that the inner braided tube can be seen; and FIG. 6 is a partial cross section of an angiographic catheter in accordance with the invention, illustrating a scarf weld through the outer layer and inner braid layer of the catheter.

BEST MODE FOR CARRYING OUT THE INVENTION

Figure 1:
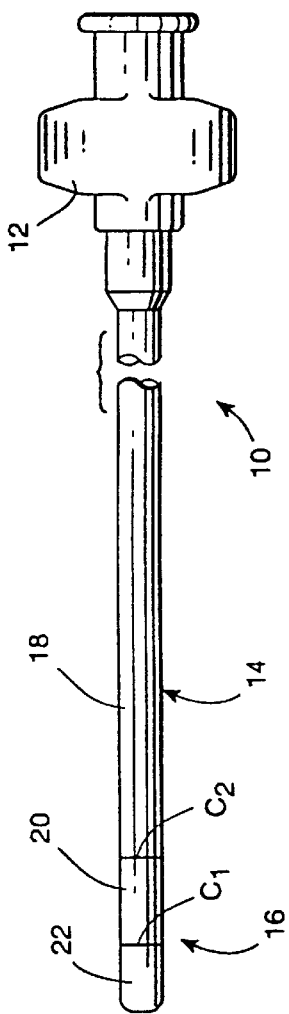
FIG. 1 is a side elevation, partly broken away, of a conventional catheter construction.
Figure 2:
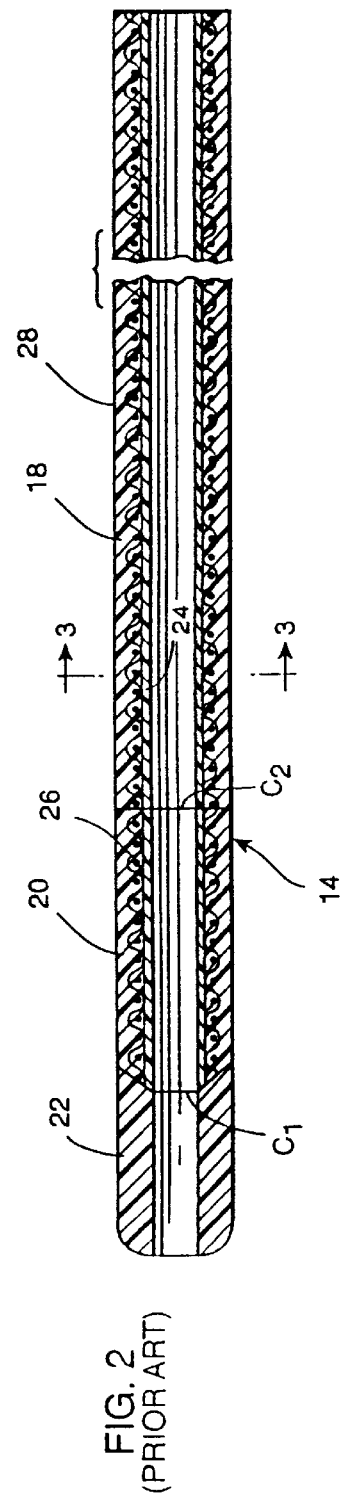
FIG. 2 is a side section of the distal end of the catheter shown in FIG. 1.
Figure 3:
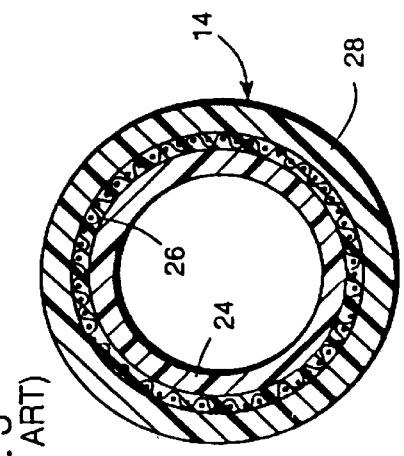
FIG. 3 is a section taken along the line 3—3 of FIG. 2.

FIGS. 1–3 represent a known catheter construction of the type disclosed in U.S. Pat. No. 5,254,107. The catheter assembly 10 includes a conventional hub 12 at its proximal end, and a tubular catheter 14 extending from the hub 12 to a distal end 16. The catheter has a first axial section 18, a second axial section 20 and a distal tip section 22.

The catheter 14 comprises an inner tubular plastic layer 24, which may be made of fluoro polymers such as PTFE, FEP or other similar polymers. A second layer 26 comprises a braided stainless steel tube applied by a conventional braiding machine. An outer, third layer 28 of plastic is applied by suitable means over the braided layer. As disclosed in the '107 patent, this outer layer may include two or more axial sections with different properties. For example, the first axial section 18 may be made of a plastic material such as nylon 12 with a Shore D durometer of about 65–70. The second axial section 20 may be Pebax, but may have a Shore D durometer of about 35–55. The tip 22 may be Pebax and may or may not be reinforced by the braided layer 26. In the '107 patent, the adjacent axial sections are butt welded or fused together, such that the joints describe circles C1 and C2 perpendicular to the longitudinal axis of the catheter.

With reference now to FIG. 4, an angiographic catheter 30 in accordance with this invention may include a relatively stiff main shaft section 32 extending forwardly from the lure fitting 34. Section 32 is axially joined at its distal end by a scarf joint to a moderately stiff, non-braided shaft extension 36 which, in turn, may be joined to a soft non-braided tip 38, again utilizing a scarf joint. The angled or scarf joints are shown at 40 and 42, respectively. The number of intermediate non-braided sections between the braided section 32 and the tip 38 may vary as required for specific applications.

FIG. 4 illustrates the inner braid layer 44 which may, in the case of an angiographic catheter, comprise the innermost layer of the catheter. For other types of catheters, such as guiding or therapeutic catheters, an innermost Teflon® (or other suitable material) layer may be employed.

Turning to FIG. 6, the scarf joint 48 between sections 32 and 36 is illustrated in detail, extending through the outer layer 46 and the inner braid layer 44. Note that the outer layer 46 is shown to have been compressed into the braid layer 44 during the shrink-fit assembly procedure mentioned above. It will be appreciated that, for some applications, an inner Teflon® layer may be employed as well, with the inner and outer layers engaged through the braid layer during shrink-fit assembly. By angling the cut 48 through the braid layer 44 as well as the outer layer 46, (such that a free end 49 of the brand layer 44 extends along and at the same acute angle as the joint 48) it is possible to achieve a more uniform or smoother transition between the axially joined sections 32 and 36 of different flexibility. In this regard, the braid layer 44 comprises, in the exemplary embodiment, annealed wire (as opposed to spring wire), insuring that the loose cut ends do not spring radially outwardly through the outer plastic layer 46. It should be appreciated, however, that it may be possible to use higher tensile strength wire in combination with suitable adhesives which would hold the loose ends in place. It will also be understood that other reinforcement configurations may be employed such as helically wrapped wire, randomly crossed wire, or other metal or non-metal or composite in fiber sleeve or strip form.

As briefly noted above, the term scarf joint in accordance with this invention is an angled joint formed at the interface of two tapered or angled cuts which do not enlarge the diameters of the components at the joint. Such joints are not, therefore, merely telescopic joints (which describe a circle (perpendicular to the longitudinal axis of the catheter at the external seam and which create double thicknesses of material), but rather, are overlap joints where each component forms mirror-image halves of the joint, and the tapered seam has an axial component along the length of the joint, with seam visible along the mated peripheral surfaces of the axially joined sections. The seam lies at an acute angle to the longitudinal axis of the catheter or lumen of the catheter. Again, the joint may be welded through the application of heat, or adhesively bonded with or without heat.

In an exemplary embodiment of the invention, the outer layer 46 of section 32 may comprise a P-Bax/Nylon blend, whereas the axially adjacent unbraided section 36 may be of moderate flexibility, comprised of P-Bax having a durometer of 50–70 D. The soft tip 38 may then be joined to section 36 as shown in FIG. 3 at scarf weld 42, or, alternatively, a non-braided shaft extension may be joined to the section 36, between the latter and the soft tip 38.

It will also be appreciated that the axially overlapped portions of the joined layers create unique intermediate or transition sections of the catheter where, for example, the tapered braid section combines with the tapered nonbraided section to create an overlapped transition area with variable flexibility, greater than the adjacent full diameter braid section 32 but not as great as the full diameter non-braid section 36. This ability to create transition lengths of with different mechanical properties or characteristics is most advantageous in areas of the catheter which will incorporate (or be bent into) curved areas. Thus, viewing the catheter as shown in FIG. 6, and assuming the catheter is bent in a clockwise direction in the area of the scarf joint 40, it will be appreciated that the overlapped seam may have a harder durometer on the outside of the curve than on the inside of the curve. As a result, not only does the scarf joint overlap area have a desirable stiffness which falls between the stiffness of the materials used to form the adjacent sections 32 and 36, but in addition, unique curve retention properties are created by reason of the dominance of the harder durometer over the softer durometer in the scarf weld transition area.

It should also be pointed out that the different catheter lengths can be of the same material but have different durometers, or they can be of different materials of the same or different durometer in order to achieve the desired flex characteristics. Additional inner and/or outer layers may be incorporated depending on the specific catheter application. Color coding between axial sections may also be used to identify sections having different properties.

With regard to the scarf joints, the seam may have an axial length to radial depth ratio of from about 3 to 1 to about 40 to 1. Short transition scarf joints provide increased surface areas which strengthens the joints, and provide longer, less abrupt transition areas than simple butt joints. Such joints minimize the tendency of kinking and provide better torque transition characteristics than conventional butt welds or joints.

Long transition scarf joints, on the other hand, also provide increased surface area for strengthening the joints. In addition, long transition scarf joints produce more desirable feel and/or handling characteristics in use. The orientation of different materials in long transition scarf joints provides ease of straightening and permits unique properties to be established within one or more curved areas of the catheter. Long transition scarf joints also allow for greater differences in durometer.

It will be appreciated that the invention extends to various catheter constructions, both diagnostic and therapeutic as well as other catheter types such as PTA, PTCA, electrophysiology, pacing leads, and so on. Suitable resins include Nylon 11 and Nylon 12; Pebax (25 D to 70 D); Nylon/Pebax blends; polyurethanes; polyethylenes, PVC and other medical grade resins and combinations thereof.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A catheter having at least two lengths of tubular material axially joined together by a scarf joint with no perceptible change in outer diameter at the scarf joint; the scarf joint including a substantially axially oriented seam component between the two lengths of tubular material with the seam visible along the peripheral surfaces of the axially joined sections and extending at an acute angle to the longitudinal axis of the catheter; and wherein one of said at least two lengths of tubular material includes an inner tubular reinforcement layer, wherein said scarf joint extends through said reinforcement layer such that said reinforcement layer has a free end extending at said acute angle, thereby conforming to said scarf joint.

2. The catheter of claim 1 wherein said two lengths of tubular material comprise two different materials with different mechanical properties.

3. The catheter of claim 1 wherein said two lengths of tubular material comprise the same material but with different durometers.

4. The catheter or claim 1 wherein said two lengths of tubular material are color coded.

5. A catheter having at least two adjacent lengths of tubular material axially overlapped and joined together by a scarf joint, said lengths having substantially identical and uniform outer diameters at and adjacent the scarf joint; the lengths of tubular material having continuous outer surfaces and a lumen extending along a longitudinal axis, the scarf joint including a seam on said outer surfaces extending more than 0.5 cm in length and at an acute angle to the longitudinal axis of the catheter such that each of the at least two adjacent lengths form substantially half of the catheter along the scarf joint, and wherein said two lengths of material are of different composition with different mechanical properties, thereby establishing an intermediate section having variable properties along said scarf joint; and wherein one of said at least two adjacent lengths of tubular material includes an inner reinforcement layer having a free end extending along said seam at said acute angle to the longitudinal axis of the catheter.

6. The catheter of claim 5 wherein said scarf joint is at least 0.5 cm long.

7. The catheter of claim 6 wherein said scarf joint is between 0.5 and 10 cm in length.

8. The catheter of claim 5 wherein a ratio of scarf joint axial length to scarf joint radial depth is from about 3:1 to about 40:1.

9. The catheter of claim 5 wherein said one of said two adjacent lengths comprises an inner braid layer and an outer plastic layer.

10. The catheter of claim 9 wherein said other of said two adjacent lengths comprises a single layer, non-braided section.

11. The catheter of claim 1 wherein said reinforcement layer comprises wire braid.

12. The catheter of claim 5 wherein said reinforcement layer comprises wire braid.

13. The catheter of claim 1 wherein said scarf joint is a welded joint.

14. The catheter of claim 1 wherein said scarf joint is an adhesive joint.

15. The catheter of claim 5 wherein said scarf joint is a welded joint.

16. The catheter of claim 5 wherein said scarf joint is an adhesive joint.

* * * * *